(12) United States Patent
Weick et al.

(10) Patent No.: US 6,686,743 B2
(45) Date of Patent: Feb. 3, 2004

(54) APPARATUS FOR MEASURING THE STATIC CHARGE OF FLOWABLE SOLIDS

(75) Inventors: John James Weick, Edison, NJ (US); Robert Olds Hagerty, La Porte, TX (US); Per K. Husby, Somerset, NJ (US); Frederick Yip-Kwai Lo, Piscataway, NJ (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 09/802,735

(22) Filed: Mar. 9, 2001

(65) Prior Publication Data

US 2002/0047712 A1 Apr. 25, 2002

Related U.S. Application Data (60) Provisional application No. 60/242,960, filed on Oct. 24, 2000.

(51) Int. Cl.[7] ............... G01N 27/02; G01R 29/12
(52) U.S. Cl. ............... 324/439; 324/457; 526/74
(58) Field of Search ............... 324/439, 457, 324/453; 430/108.8, 109.9; 526/74; 585/12

(56) References Cited

U.S. PATENT DOCUMENTS

| | | |
|---|---|---|
| 2,421,430 A | 6/1947 | Ott |
| 3,225,299 A | 12/1965 | Middendorf |
| 3,406,344 A | 10/1968 | Hopper |
| 3,544,889 A | 12/1970 | Alauzet et al. |
| 3,627,682 A * | 12/1971 | Hall, Jr. ............... 430/108.9 |
| 3,727,125 A | 4/1973 | Mourier ............... 324/32 |
| 3,764,894 A * | 10/1973 | Dukek ............... 324/453 |
| 3,943,437 A | 3/1976 | Mourier ............... 324/32 |
| 4,010,366 A * | 3/1977 | Neukermans et al. ....... 250/282 |
| 4,063,153 A | 12/1977 | Dechene et al. ............... 324/30 |
| 4,074,184 A | 2/1978 | Dechene et al. ............... 324/30 |
| 4,082,994 A | 4/1978 | Newton ............... 324/30 |
| 4,291,273 A | 9/1981 | Dechene et al. ............... 324/343 |
| 4,309,661 A | 1/1982 | Kamoto ............... 324/453 |
| 4,455,532 A | 6/1984 | Gregory et al. ............... 324/457 |
| 4,607,228 A | 8/1986 | Reif ............... 324/454 |
| 4,619,145 A | 10/1986 | Girgenti ............... 73/861.04 |
| 4,714,890 A | 12/1987 | Dechene et al. ............... 324/454 |
| 4,904,944 A | 2/1990 | Dechene et al. ............... 324/454 |
| 5,022,274 A | 6/1991 | Klinzing et al. ............... 73/861.04 |
| 5,450,005 A * | 9/1995 | Peterson, Jr. ............... 324/457 |
| 5,541,518 A | 7/1996 | Babbitt et al. ............... 324/454 |
| 5,650,254 A * | 7/1997 | Eguchi et al. ............... 430/108.8 |

FOREIGN PATENT DOCUMENTS

| | | | |
|---|---|---|---|
| FR | 2733045 A | | 10/1996 |
| GB | 1586477 A | | 3/1981 |
| JP | 56-46249 | * | 4/1981 |
| JP | 09329583 | * | 12/1997 |

OTHER PUBLICATIONS

Ruckdeschel et al., *Contact electrification between insulators: Phenomenological aspects*, 46 Jol Applied Phys. 4416–4430 (Oct. 1975).

(List continued on next page.)

*Primary Examiner*—Walter E. Snow
*Assistant Examiner*—Donald M Lair
(74) *Attorney, Agent, or Firm*—Osborne K. McKinney (57) ABSTRACT

An apparatus for measuring and a method for controlling the static charge developed by a flowable solid as it passes through a conduit. The flowable solid is conveyed through the conduit in such a manner that the powder develops a static charge due to the triboelectric effect as it moves against the conduit walls. The static charge on the solid is then measured using a static charge measuring device such as a Faraday drum or cage.

12 Claims, 6 Drawing Sheets

OTHER PUBLICATIONS

Yamamoto et al., *Triboelectric Charging of Polymer Particles by Impact*, 3 Part. Charact. 117–121 (1986) (no month given).

Peterson, *Contact Charging beween Nonconductors and Metal*, 25 Jol. App. Phys. 907–915 (Jul. 1954).

Chubb et al., *Comparative Studies On Methods Of Charge Decay Measurement*, 30 Jol. Electrostatics 273–283 (1993).

Kunkel, *The Static Electrification of Dust Particles on Dispersion into a Cloud*, 21 Jol. App. Phys. 820–832 (Aug. 1950).

Patent Abstracts of Japan, vol. 009, No. 090 (P–350), Apr. 19, 1985 & JP 59 217157 A (Sankiyou Dengiyou KK), Dec. 7, 1984 abstract.

Patent Abstracts of Japan, vol. 008, No. 215 (P–305), Oct. 2, 1984 (Oct. 12, 1984) % JP 59 100855 A (Sankiyou Dengiyou KK), Jun. 11, 1984 abstract.

Krupa A. et al., *A Method for Aerosol Particle Charge Measurements*, Journal of Electrostatics, Elsevier Science-publishers B.V. Amsterdam, NL, vol. 23, No. 1, Index, Apr. 1, 1989 pp. 283–292, XP000046276.

* cited by examiner

APPARATUS FOR MEASURING THE STATIC CHARGE OF FLOWABLE SOLIDS

This application claims the benefit of Provisional Application No. 60/242,960, filed Oct. 24, 2000.

FIELD OF THE INVENTION

The invention relates to an apparatus for measuring the static charge developed by a flowable solid as it passes through a conduit. The apparatus comprises a receptacle for receiving a sample of a flowable solid, a conduit for conveying the flowable solid and a device for measuring the static charge of the flowable solid as it exits the conduit. A method for measuring the static charge of a flowable solid is also provided.

BACKGROUND OF THE INVENTION

A common problem in industry has been the processing and handling of flowable solids. Because of their high surface area-to-mass ratio and other factors, they have a tendency to develop electrostatic charges, particularly when they are conveyed through pipes or other conduits. The electrostatic charges cause the flowable solids to collect on contiguous surfaces. This phenomenon reduces the efficiency and accuracy of their conveyance. On occasion, charges can develop to an extent that spontaneous electrical discharges can occur. The discharges can lead to damage of equipment and storage containers as well as injury to personnel. Testing of the propensity of a flowable solid to develop a static charge as well as the nature of the charge developed can lead to the development of systems to improve the conveyance of flowable solids without the development of static charges.

The principal cause for static charge generation when a flowable solid is conveyed through a conduit is frictional contact of dissimilar materials by a physical process known as the triboelectric effect. As the flowable solid passes through the conduit, static is generated by frictional contact between the flowable solid and the walls of the conduit. The frictional contact causes a flow of electrical charges from the walls of the conduit to or from the flowable solid.

Static charges also present problems in olefin polymerization processes. It is well known that in fluidized bed polymerization reactors, static charges often develop as a result of frictional contact between the growing polymer particles and the metal walls of the reactor. Static charges also develop on the dry catalyst particles as they are injected into the reactor. The catalyst is normally injected using nitrogen or other inert gases to convey the catalyst through a small stainless steel tube into the reactor. As the catalyst passes through the tube, friction between the catalyst and the wall of the tube generates a charge on the catalyst, which then influences the static charge on the fluidized bed.

Static charges in a fluidized bed reactor are known to contribute to a phenomenon known as sheeting. By "sheeting" is meant the adherence of fused catalyst and resin particles to the walls of the reactor. The sheets will eventually dislodge from the wall and, if the sheets are large enough, they can result in reactor plugging. A related phenomenon called "drooling" or dome sheeting occurs when sheets of molten polymer form on the reactor walls, usually in the expanded section or "dome" of the reactor, and flow along the walls of the reactor and accumulate at the base of the reactor. This can result in plugging of the distributor plate in the reactor and loss of fluidization.

By knowing the size and polarity of the charge that a catalyst particle develops during injection, steps can be taken to neutralize the charge before sheeting occurs. One method of controlling the charge is through the use of static control agents. Timely addition of an effective amount of these agents has proven to be effective in reducing sheeting. Thus it would be helpful to know the nature of the static charge that a catalyst develops when it is injected into a reactor.

Some systems have been developed to measure static charges of flowable solids. Some of these involve the testing of the flowable solids themselves before they are introduced into a conduit or conveyance system. One such system is described in Ruckdeschel et al., *Contact Electrification Between Insulators: Phenomenological Aspects*, 25 Jol. Applied Phys. 4415 (1975). In this article the authors placed a sample of a flowable solid in a cylindrical Faraday cage. The cage was then rolled, and the charge developed by the flowable solid as it rolled inside the cage was measured. Another method involved firing a sample of polymer with a pneumatic gun, with the polymer striking a metal plate. Yamamoto, *Triboelectric Charging of Polymer Particles by Input*, 3 Part. Charact. 117–121 (1986). The deflected polymer was captured in a Faraday drum and the charge on the particle was measured. Neither of these systems duplicates the environment actually encountered by a flowable solid when it is conveyed through a conduit.

The study of electrostatic charges of flowable solids has been done with devices, which involve the use of moving parts. See, e.g., U.S. Pat. Nos. 2,421,430; 3,225,299; 3,406,344; 3,544,889; 3,727,125; and 3,943,437. Peterson, *Contact Charging Between Nonconductors and Metal*, 25 Jol. App. Phys. 907–915 (1954). Chubb et al., "Comparative Studies on Methods of Charge Decay Measurement," 50 Jol. Electrostatics 273 (1993).

Similarly, work has been done to measure the static charge of flowable solids using complex detectors or conveying mechanisms. These include the use of a photographic representation of the charge on a flowable solid, Kunkel, *The Static Electrification of Dust Particles on Dispersion Into a Cloud*, 121 Jol. App. Phys. 820–832 (1988).

Efforts have been made to develop simpler devices; however, the efforts do not measure the static charge developed on a flowable solid as it moves through a conduit. The work to date has involved the use of a by-pass line, U.S. Pat. No. 4,309,661; a deflecting metallic screen which is placed between the flowable solid and a static probe, See U.S. Pat. No. 5,541,518; and by measuring the static charge on the effected tube itself. Other devices are directed to using the static charge to determine other parameters such as solids density in the conveyance stream. See, e.g., U.S. Pat. Nos. 4,063,153; 4,074,184; 4,291,273; 4,082,994; 4,619,145; 4,714,890; 4,904,944; 4,607,228; and 5,022,274.

A need still exists for a simple device that can directly measure the static charge that a flowable solid, such as a supported catalyst, develops as it passes through a conduit.

SUMMARY OF THE INVENTION

The apparatus of the present invention comprises a receptacle for receiving a sample of a flowable solid, a conduit for conveying a flowable solid and a device for measuring the static charge of the flowable solid as it leaves the conduit. Additionally, a pressurized gas delivery system can be used to help convey the flowable solid through the conduit, thereby simulating actual commercial conditions.

In practice, a sample of a flowable solid to be tested is placed in a receptacle at one end of a conduit. The flowable solid is then conveyed through the conduit in such a way that static charge develops on the flowable solid. Usually, this involves conveying the flowable solid through the conduit using an inert pressurized gas. The conduit should be of sufficient length and diameter to promote the development of a static charge on the flowable solid. Additionally, the conduit should be constructed of the same materials as the conduit being modeled. As the flowable solid exits the conduit, it enters a device capable of measuring the static charge on the flowable solid. The preferred device is a Faraday drum of the type described below.

The Faraday drum represents an application of a fundamental measurement technique named after Michael Faraday, a British physicist and chemist (1791–1867). The system operates on the principal of displaced current. Because the inner drum of the Faraday system is connected to ground through a low resistance current measuring device, the voltage on the inner drum must be zero. When charged flowable solid enters the Faraday drum, an electrical charge is displaced from the Faraday drum through a current measuring device to ground, as required to keep the overall system voltage zero. The amount of charge displaced to ground is equal and opposite to the charge that enters the drum with the resin and catalyst particles. The current flow is recorded and integrated over the time period that the particles are introduced to the system to provide a quantitative measurement of the charge.

In practice, the actual measurement taken is the current that flows from ground to the drum, which is opposite in sign to the current that flows from the drum to ground. In effect, the current meter is connected backwards to provide a sign inversion to the measurement. In this way, the measured current, integrated over time, is exactly equal to the charge that enters the system, both in magnitude and sign.

The preferred means of measuring the current flow is with an electrometer, such as a Keithley Model 610C. These devices provide the dual capability of measuring and integrating the current as required by the Faraday technique. Other devices to measure and integrate the current can be employed, as known by those skilled in the art. For example, the current can be measured with a simple current meter (ammeter), with the readings recorded and digitally integrated over time to provide the required charge measurement.

There is also provided a method for determining the static charge developed by a flowable solid as it is conveyed through a grounded conduit. The method involves introducing a sample of flowable solid into one end of a conduit, conveying the polymer sample through the conduit in a manner sufficient to promote the development of a static charge on the flowable solid and measuring that static charge on the flowable solid as it exits the conduit. The method may also involve the introduction of a gas into the conduit to help convey the flowable solid through the conduit.

The apparatus and method of the invention provide a relatively simple and direct method for measuring that static charge developed by a flowable solid when it passes through a conduit. Information developed using this device and method can be used to design systems to prevent static charge development, as well as a means for monitoring static charge development in commercial systems.

DETAILED DESCRIPTION OF THE INVENTION

In its simplest form, the present invention comprises a conduit for transporting a flowable solid and a device for measuring the static charge on a flowable solid. The device for measuring the static charge is positioned at one end of the conduit such that it receives any flowable solids that exit the conduit. The conduit should be of sufficient length to promote the development of static charges on the flowable solid and the flowable solid should be conveyed at a sufficient rate to induce the development of such charges. Preferably, the flowable solid should be conveyed through the conduit at a rate that is the same as the rate that would be used for commercial operations. Similarly, the diameter of the conduit should be the same as the commercial device being evaluated. The conduit should also be constructed of the same material as the conduit used in commercial practice.

Figure 1:
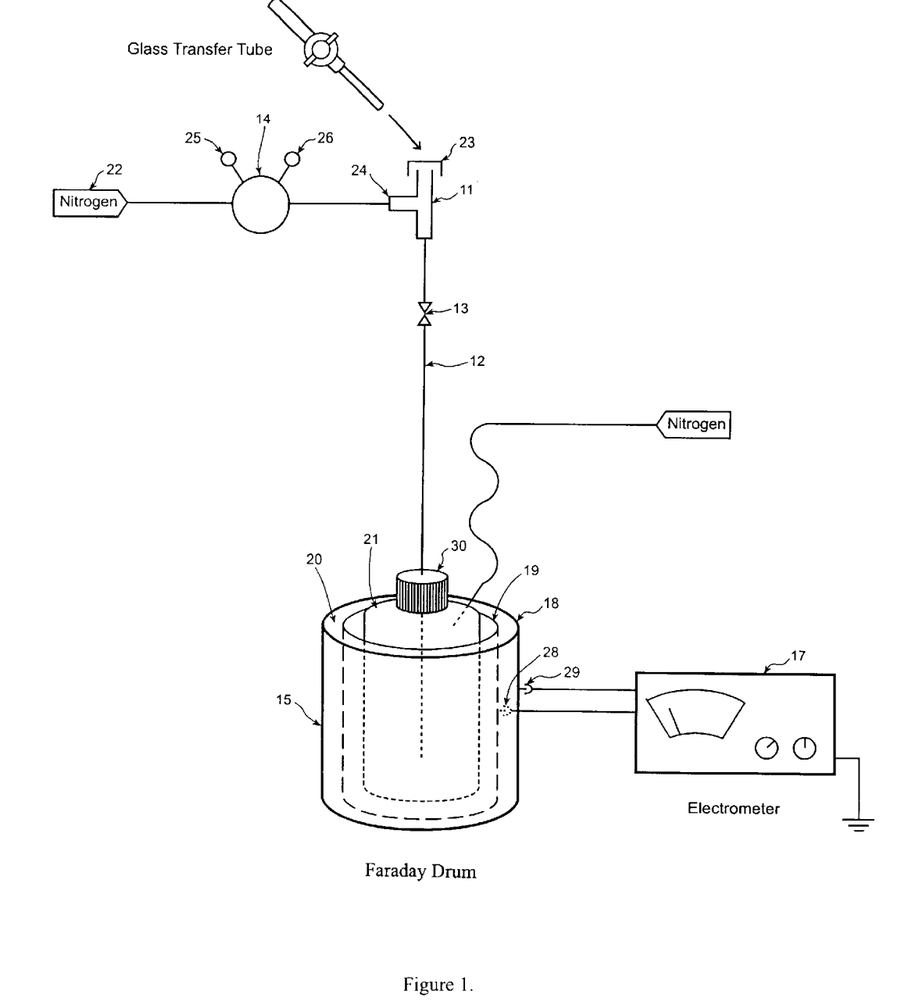
FIG. 1 is a diagram of an electrostatic charging device of the present invention.

Referring to FIG. 1, a simple device for practicing the invention is shown. The device comprises a receptacle, 11, at one end of a conduit, 12. The receptacle, 11, is separated from the conduit, 12, by means of a valve, 13, which prevents the flowable solid to be tested from prematurely flowing into the conduit, 12. The receptacle, 11, may also have a gas delivery system, 14, connected to it to provide a source of pressurized gas to convey the flowable solid through the conduit, 12. At the distal end of the conduit, 12, is located a static measuring device, 15. The static measuring device, 15, is capable of capturing the flowable solid as it exits the conduit, 12, and then measuring the static charge on the flowable solid.

If the conduit is constructed of metal, it is important that it be electrically connected to ground. Otherwise, the solids passing through the conduit would induce an electrical charge on the conduit, which would produce a distortion of the measurements. The electrical connection to ground may be accomplished through the use of a grounding wire attached to the conduit by an alligator clip.

The conduit used in the embodiment shown in FIG. 1 is a 0.32 cm diameter stainless steel tube, which is approximately 1.1 meters long. Other tube length and diameters may be used as long as they are sufficient length and diameter to induce the development of static charges in the flowable solid being evaluated.

Flowable solids that can be evaluated using the present invention include, but are not limited to, silica particles, catalysts, carbon black, asbestos, glass, mica, nylon, metals, various polymer particles, sugar and the like. Any particulate matter that can develop a static charge when conveyed through a conduit can be evaluated using the present invention.

In the embodiment shown in FIG. 1, the receptacle, 11, is a tee fitting, attached to the conduit by means of a globe valve. The upper end of the tee is closed with a plug, 23. The side leg of the tee, 24 is connected to a source of pressurized gas. In the specific embodiment, the tee is connected to a gas regulator, 14, which in turn is connected to a cylinder of nitrogen, 22. Other means of supplying gas to convey the flowable solid will be readily apparent to those skilled in the art.

In the specific embodiment shown in FIG. 1, the static measuring device, 15, is a Faraday drum connected to an electrometer, 17. The Faraday drum, 15, comprises an outer shielding drum, 18, an inner drum, 19, and an insulating layer, 20, between said inner and outer drums. The insulating layer should consist of a non-conductive material such as Teflon™. Alternatively, it may comprise an air gap between the two drums. In either event, the two drums should be electrically isolated from each other. Both the inner and outer drums should be made of an electrically conductive material such as metal. In the preferred embodiment, the drums are made of steel.

A flowable solid receiving container, 21, is located inside the inner drum, 19. The flowable solid receiving container, 21 should be capable of venting the gas used to transport the flowable solid while retaining substantially all the flowable solid being studied. The container, 21, should not interfere with the flowable solid inducing an electric charge in the inner drum, 19. In the embodiment shown, the flowable solid receiving container, 21, consists of a thin walled (approximately 0.16 cm) polyethylene bottle. The bottle's cap, 30, is perforated with numerous 0.25 cm diameter holes and the cap is secured with glass wool. This configuration allows excess pressure to escape from the bottle while retaining the flowable solid in the bottle. A 0.32 cm hole is placed in the center of the cap, 30, to allow the conduit to pass through the cap into the bottle. The conduit should extend through the cap into the bottle to such a depth that the conduit comes within 2.5 cm of the bottom of the bottle.

An electrometer, 17, is used to measure the charge induced in the inner drum, 19, by the charged flowable solid. The electrometer is connected to the inner drum by means of a first conductive bolt, 28, connected to the inner drum, 19. While the first conductive bolt, 28, passes through the outer shield drum, 18, it is electrically isolated from the outer drum, 18, by means of an insulating coating such as Teflon™. This first conductive bolt, 28, is then connected to the negative input of a standard electrometer, 17, making the inner drum, 19, a negative electrode. A second conductive bolt, 29, is attached to the outer drum, 19, in such a manner that it pierces the outer drum but does not contact the inner drum. This second conductive bolt, 29, is then attached to the positive input of the electrometer described above making the outer drum a positive electrode. The electrometer used in the embodiment shown in FIG. 1, was a Keithley Model 6512 internally grounded electrometer. It will be readily apparent to those skilled in the art that other means for attaching the electrometer to the Faraday drum can be used as well as other makes and models of electrometers.

As noted above, an electrometer is the preferred means of measuring current flow caused by the introduction of the charged flowable powder into the Faraday drum; however, other means of measuring the charge flow can be used. For example, the current can be measured with a simple current meter (ammeter), with the readings recorded and digitally integrated over time to provide the required charge measurement.

The apparatus described above can be used in the following manner. A sample of a flowable solid is introduced into the receptacle and the receptacle is then closed with the plug. A baseline reading is then taken on the electrometer and recorded. The gas pressure system is then opened to allow the pressurized gas into the receptacle. The globe valve is then opened to allow the gas to convey the flowable solid through the conduit and into the flowable solid-receiving container. The electrostatic charge that develops as a result of the flowable solid passing through the conduit induces an opposite charge in the Faraday drum which causes flow of current from the ground, through the electrometer, to the Faraday drum.

The gas used in the practice of the invention should be the normal gas or gases used to convey the flowable solid being measured. For example, certain catalyst compositions are sensitive to moisture and oxygen requiring the use of an inert gas, such as nitrogen. Additionally, when such materials are tested, a constant purging of the system with the inert gas at low pressure is desirable.

The apparatus of the invention can also be used to evaluate the effectiveness of various materials in preventing or neutralizing the static charge developed by a flowable solid when it is conveyed through a conduit.

It is known that difference materials will develop different charges when they rub against each other. Some materials such as glass or nylon tend to charge positively whereas other materials such as Teflon™ and polyvinyl chloride tend to charge negatively. Materials can be grouped according to their tendency to charge either positive or negative. This grouping is known as a Triboelectric Series. When materials at different ends of the triboelectric series are combined and then conveyed through a conduit, the charges developed tend to balance each other. For example, when an olefin polymerization catalyst which generally shows a negative charge when conveyed through a conduit is mixed with a material such as carbon black or aluminum, which is at the opposite end of the triboelectric series, a neutral or slightly positive charge is measured. Thus by combining two flowable solids in the appropriate proportions, the static charge developed can be controlled. The present invention provides a simple and accurate way to determine which combination of materials will yield a mixture which will have an essentially neutral charge when conveyed through a conduit.

As used in this application, the phrase olefin polymerization catalyst refers to catalyst systems useful in the polymerization of olefins to polyolefin. Examples of these include chromium-based catalysts such as those described in U.S. Pat. No. 4,532,211; traditional Ziegler-Natta catalyst systems such as those described in U.S. Pat. Nos. 4,803,257 and 5,391,657 as well as metallocene catalyst systems such as those described in U.S. Pat. Nos. 4,530,914, 4,871,705, 4,937,299, 5,017,714, 5,055,438, 5,096,867, 5,120,867, 5,124,418, 5,198,401, 5,210,352, 5,229,478, 5,264,405, 5,278,264, 5,278,119, 5,304,614, 5,324,800, 5,347,025, 5,350,723, 5,384,299, 5,391,790, 5,391,789, 5,399,636, 5,408,017, 5,491,207, 5,455,366, 5,534,473, 5,539,124, 5,554,775, 5,621,126, 5,684,098, 5,693,730, 5,698,634, 5,710,297, 5,712,354, 5,714,427, 5,714,555, 5,728,641, 5,728,839, 5,753,577, 5,767,209, 5,770,753 and 5,770,664 all of which are herein fully incorporated by reference.

In combining the materials, the added flowable solid should be such that it does not adversely impact the utility of the first material. For example, any material added to a catalyst should not affect the catalytic ability of the catalyst. Inert, flowable solids such as carbon black and alumina, are well known to those skilled in the art.

One particularly useful application of this phenomenon is in the field of olefin polymerization, particularly fluidized bed olefin polymerization. As noted above, the development of static charges in a fluidized bed reactor can lead to sheeting, which in turn negatively impacts the reactor efficiency. One of the features that appears to contribute to this phenomenon is the static charge induced in the catalyst when it is injected into the reactor. For example, when a metallocene catalyst is injected into a fluidized bed reactor, it usually develops a negative charge.

It has been observed that by combining the catalyst with a material at a different place in the triboelectric series, the charge that develops on the catalyst is reduced, and in some cases reversed. For example, when a metallocene catalyst is combined with a positive charge-inducing material such as alumina or carbon black, the charge induced when the catalyst was conveyed through a conduit was significantly lower than when the catalyst alone was conveyed through the conduit. By using the apparatus of the present invention, the correct proportion of the alumina or other positive charge-inducing material needed to bring the overall charge to zero can be determined.

Another application is in the design of systems to convey flowable solids. Different conditions such as conduit construction, and gas flow rates can be tested to determine what conditions will yield powders with the least static charge while assuring that the system meets the desired specifications.

EXAMPLES

A series of experiments were run to evaluate the size and nature of the static charge a flowable solid develops when conveyed through a tube. In each example, a sample of a flowable solid was introduced into a chamber or receptacle similar to that described above. The receptacle was then pressurized with nitrogen. When the valve at the bottom of the receptacle was opened, the flowable solid was then forced through the conduit into a Faraday drum where the charge induced by the flowable solid was measured.

Example 1

Figure 2:
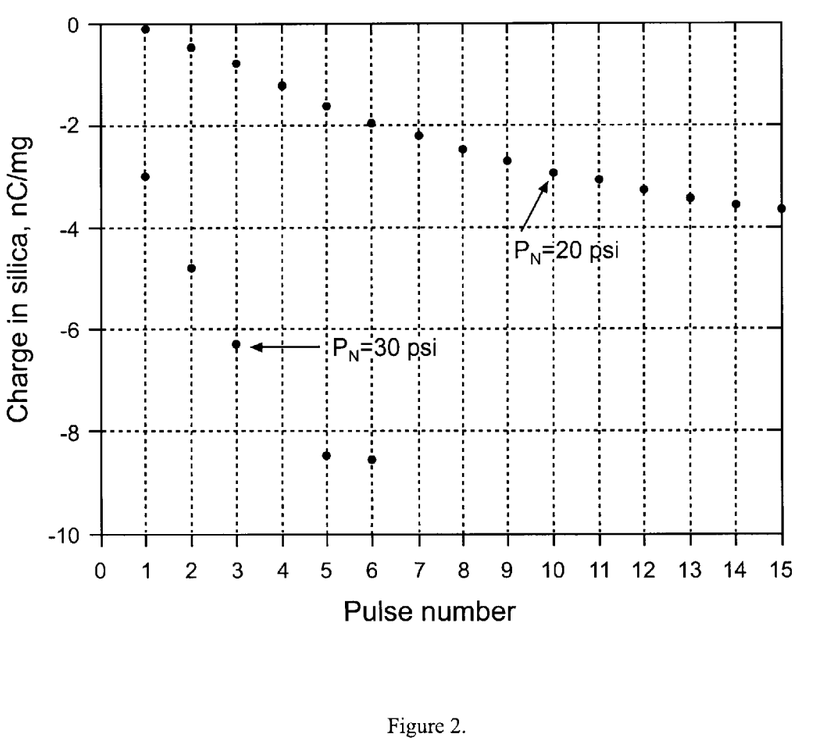
FIG. 2 is a plot of the static charge developed when a sample of silica is conveyed through a steel conduit at 138 kPa (20 Psi) and 207 kPa (30 Psi).

A commercial grade of silica, ES-70 manufactured by Crosfield, was tested in the apparatus described above. The silica had previously been dehydrated by heating it to 700° C. for 4 hours under a nitrogen atmosphere. The silica was loaded into the receptacle and the receptacle was sealed with a rubber septum. The receptacle was then charged with 138 kilopascals of nitrogen. A valve at the bottom of the receptacle was opened for approximately 0.5 seconds, which allowed the silica to pass through a 1.1 meter, 0.3 cm diameter stainless steel tube. The charge developed on the silica was then measured as described above. The receptacle was then recharged with nitrogen and the process repeated 15 times until the receptacle was empty. The charge developed on the silica was measured in nanocoulombs and then divided by the amount of silica introduced into the receptacle to yield a reading in nanocoulombs per milligram of silica ($\eta C/mg$). The results are shown in FIG. 2. The measured static charge increased with each nitrogen pulse until an asymptotic limit was reach beyond which there was no further increase in the static charge. The total static charge measured after 15 pulses of nitrogen was $-3.7$ $\eta C/mg$.

Example 2

In Example 2, the same conditions as Example 1 were used except that the nitrogen pressure was increased to 207 kilopascals. FIG. 2 shows the static charge measured from each pulse of nitrogen through the conduit. The measured static charge increased with each nitrogen pulse until an asymptotic limit was reached, beyond which there was no further increase in static charge. The total static charge measured after 6 pulses of nitrogen was $-8.6$ $\eta C/mg$. The higher magnitude of charge compared with Example 1 demonstrates the effect of the higher conveying velocity that resulted from the higher nitrogen pressure.

Examples 3 and 4

In Example 3, a sample of the same type of silica used in examples 1 and 2 was injected through a 0.3 cm diameter tube under a nitrogen pressure of 206.84 kilopascals. The nitrogen pulses were repeated 20 times with no additional catalyst added.

In Example 4, the same conditions as Example 3 were employed except that a 0.6 cm diameter stainless steel conduit was used.

Figure 3:
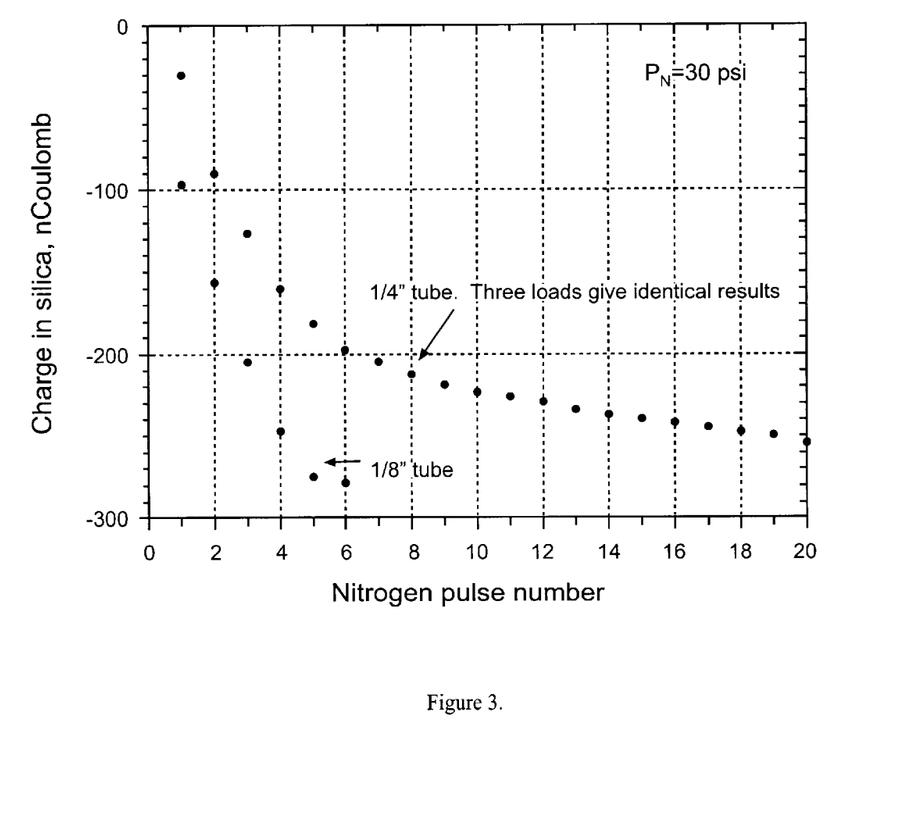
FIG. 3 is a plot of the static charge developed when a sample of silica was conveyed through steel conduits of different diameters at 207 kPa.

FIG. 3 shows a comparison of the charges developed on the silica when the different diameter conduits are used.

Examples 5 and 6

In these examples, the silica used above was injected through a 0.3 cm stainless steel conduit (Example 5) and through a 0.3 cm high density polyethylene conduit (Example 6). In both examples, the nitrogen pressure was 207 kilopascals.

Figure 4:
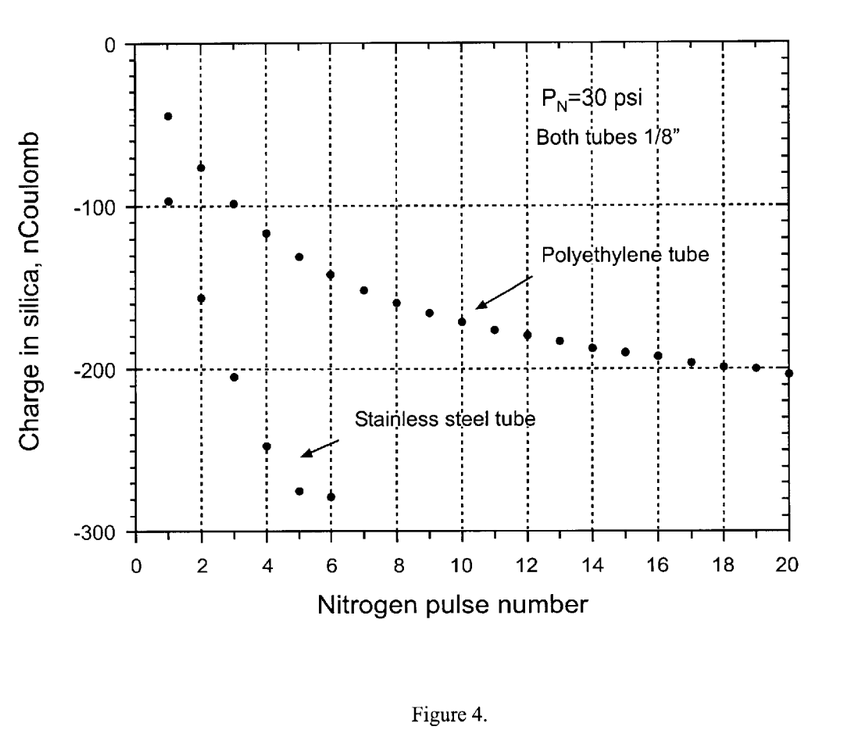
FIG. 4 is a plot of the static charge developed when a sample of silica was conveyed through a steel conduit and a high density polyethylene conduit at 207 kPa.

FIG. 4 reports the static charge development after 20 pulses for Example 6 and six pulses for Example 5.

Examples 7 and 8

In Example 7, a sample of the silica described above was injected through a 0.3 cm, 1.1 meter stainless steel conduit with 69 kilopascals nitrogen. The charge measure for the first pulse was recorded. This was repeated for 10 loads of silica.

In Example 8, the above experiment was repeated except the Davidson 955–600 silica was used. The silica had been previously dehydrated by heating to 600° C. under a nitrogen atmosphere.

Figure 5:
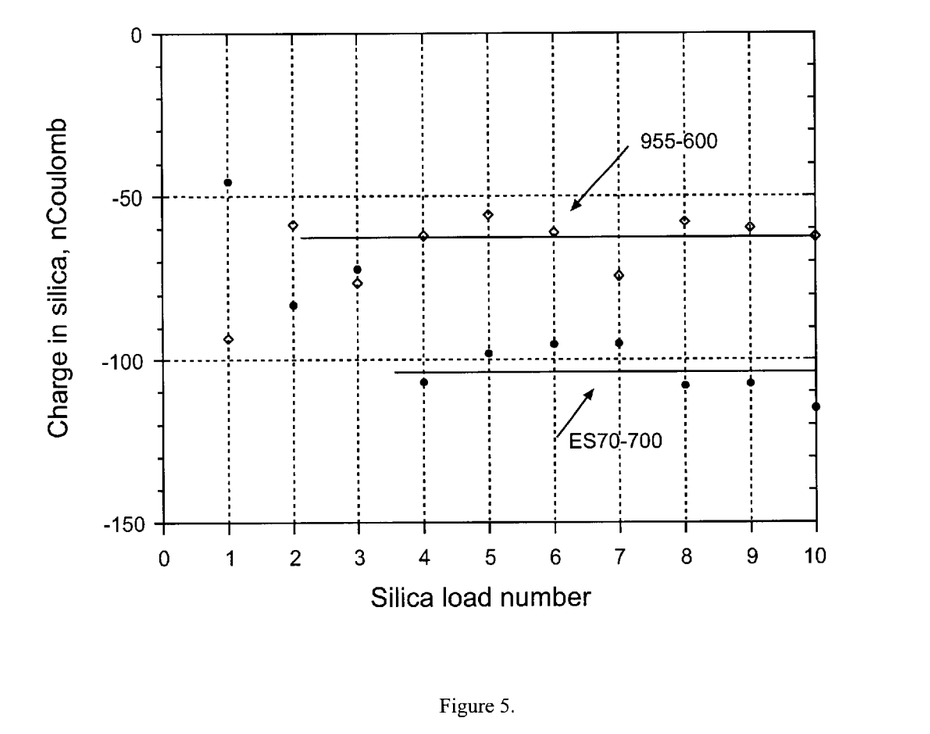
FIG. 5 is a plot of the static charge developed by two different samples of silica when conveyed through a steel conduit at 69 kPa (10 Psi).

The static charge developed by the silica for each is reported in FIG. 5.

Example 9

In this example, the static charge developed by a silica supported catalyst is compared with the same catalyst mixed with the 2% by weight of alumina.

First, a sample of dry catalyst was loaded into the apparatus as described above. A charge of 207 kilopascals of nitrogen was used to convey the catalyst through a 1.1 meter, 0.3 cm diameter stainless steel conduit. This process was repeated 16 times until there was no further increase in the measured static charge.

Figure 6:
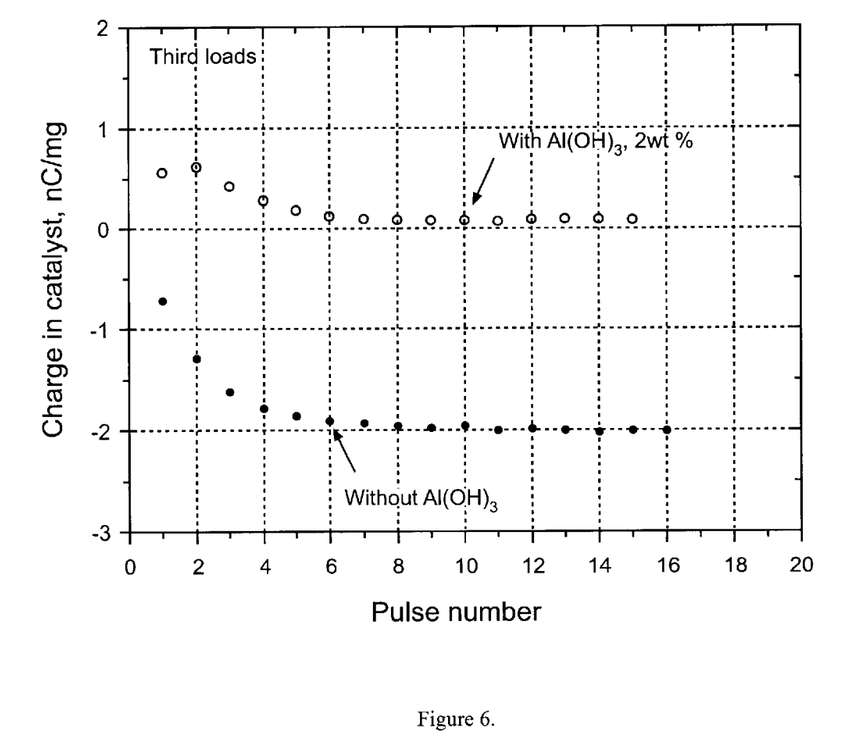
FIG. 6 is a plot of the charge developed by a silica supported metallocene catalyst alone and when the catalyst is mixed with alumina and then conveyed through a stainless steel conduit at 207 kPa.

Next, a portion of the same catalyst mixed with 2 wt % alumina was conveyed through the conduit under the same conditions, with the exception that 20 pulses of nitrogen were used. The static charges measured after each pulse are recorded in FIG. 6.

As seen from the examples above, the apparatus of the present invention is useful in measuring the static charge developed by a flowable solid under a variety of flow conditions. Other applications of the apparatus and method of the invention will be apparent to those skilled in the art.

What we claim is:

1. An apparatus for measuring the electrostatic charge on a flowable solid comprising:
   a. a flowable solid sample receptacle;
   b. a static charge measuring device; and
   c. a conduit for conveying the flowable solid from the receptacle to the static charge measuring device;
   wherein the conduit is grounded,
   the static charge measuring device comprises a Faraday drum which comprises:
   e. an outer drum;
   f. an inner drum;
   g. an insulating layer between the inner and outer drum; and
   h. a current measuring device connected to said inner drum; and
   said flowable solid comprises a mixture of two or more flowable solids, each flowable solid having a different triboelectric effect on the conduit.

2. A method for controlling the static charge in an olefin polymerization developed by a flowable powder as it passes through a conduit comprising mixing the flowable powder with a second inert flowable powder which develops an opposite static charge when said second powder passes through a conduit, wherein the conduit of the first flowable powder is used in the olefin polymerization.

3. The method of claim 2 wherein said first flowable powder is an olefin polymerization catalyst.

4. The method of claim 3 wherein said olefin polymerization catalyst is a metallocene catalyst.

5. The method of claim 2 wherein said second inert flowable powder is selected from the group comprising alumina and carbon black.

6. The method of claim 2 wherein a pressurized gas is used to convey the first flowable powder.

7. The method of claim 6 wherein the pressurized gas is nitrogen.

8. The method of claim 2 wherein each flowable solid has a different triboelectric effect on the conduit.

9. The method of claim 8 wherein the second flowable powder has the effect of reducing or neutralizing the static charge of the first flowable powder that is developed when the first flowable powder passes through the conduit.

10. The method of claim 2 wherein the conduits are grounded.

11. The method of claim 2 wherein the olefin polymerization is a fluidized bed olefin polymerization.

12. The method of claim 2 wherein the conduit of the first flowable powder is used to inject the powder into the polymerization reactor.

* * * * *

UNITED STATES PATENT AND TRADEMARK OFFICE
CERTIFICATE OF CORRECTION

PATENT NO. : 6,686,743 B2
DATED : February 3, 2004
INVENTOR(S) : Weick et al.

It is certified that error appears in the above-identified patent and that said Letters Patent is hereby corrected as shown below:

Column 6,
Line 35, "aluminum," should be deleted, and -- alumina, -- inserted therefore.

Signed and Sealed this

Eighteenth Day of January, 2005

JON W. DUDAS
*Director of the United States Patent and Trademark Office*